United States Patent [19]

Sumino

[11] Patent Number: 4,487,073
[45] Date of Patent: Dec. 11, 1984

[54] ULTRASONIC SYSTEM

[75] Inventor: Yoichi Sumino, Ootawara, Japan

[73] Assignee: Tokyo Shibaura Denki Kabushiki Kaisha, Kawasaki, Japan

[21] Appl. No.: 460,941

[22] Filed: Jan. 25, 1983

[30] Foreign Application Priority Data

Mar. 15, 1982 [JP] Japan ................. 57-41523

[51] Int. Cl.³ .......................... G01N 29/00
[52] U.S. Cl. ...................... 73/626; 73/625
[58] Field of Search ............. 73/626, 625; 367/105; 310/369

[56] References Cited

U.S. PATENT DOCUMENTS

| 4,012,952 | 3/1977 | Dory | 73/626 |
| 4,155,259 | 5/1979 | Engeler | 73/626 |
| 4,169,385 | 10/1979 | Kellogg et al. | 73/610 |
| 4,242,913 | 1/1981 | Mezrich et al. | 73/626 |
| 4,307,613 | 12/1981 | Fox | 73/626 |

OTHER PUBLICATIONS

"Transient Fields of Concave Annular Arrays", Ultrasonic Imaging 3, 37–61 (1981), Marcel Arditi, F. Stuart Foster, John W. Hunt.

Primary Examiner—Stephen A. Kreitman
Assistant Examiner—John E. Chapman, Jr.
Attorney, Agent, or Firm—Oblon, Fisher, Spivak, McClelland & Maier

[57] ABSTRACT

An ultrasonic system for non-destructive testing in industry and for visualizing soft tissue structure in medical diagnosis using a coaxial transducer array formed of a plurality of annular transducer elements each having the same predetermined area. The area of each of the transducer elements and the radiating aperture of the array is chosen to provide a well-resolved narrow beam in accordance with the focal length along the axis of the array.

2 Claims, 8 Drawing Figures

ULTRASONIC SYSTEM

BACKGROUND OF THE INVENTION

1. Field of the Invention

This invention relates to an ultrasonic system including a flat annular transducer array constructed of a plurality of concentric rings in a common plane, in which the rings are connected to a transmitter and a receiver through a delay network which serves to delay transmitted and received electrical energy transmitted to or received by the rings of the transducer by progressively different time delays and, more particularly, to an ultrasonic system optimizing the transducer characteristics and improving the lateral resolution in the focal region of the transducer.

2. Description of the Prior Art

The lateral resolution of acoustical images depends primarily on the ultrasonic beam width. A known method of reducing the width of the ultrasound beam by electronic focusing is described in U.S. Pat. No. 4,169,385 issued in the names of Seeley C. Kellogg, Philip J. Peluso and Richard B. Bernadi on Oct. 2, 1979. It discloses an ultrasonic imaging system including an annular transducer array in which the elements of the transducer are energized at progressively different times to generate the desired shape of the beam. For example, as illustrated in FIG. 1, to focus at the focal length f, on the axis, the time delay Tp at any point P being distant x from the axis 1 of the array is given by:

$$Tp = f/c[\{1+(r_n/f)^2\}^{\frac{1}{2}} - \{1+(x/f)^2\}^{\frac{1}{2}}]$$

where $r_n$ is the outer radii of the outmost n-th ring of the array, and c is the velocity of the ultrasonic wave.

Equation (1) shows that the time delay varies continuously as a function of the distance x between any point P and the axis 1. In practice, the annular transducer array includes a certain finite number of discrete ring elements, and all the elements have equal widths, so that the time delay introduced by the delay lines varies inversely as a discontinuous function of off axis distance and still operates to increase sidelobe amplitudes.

Attempts to make small the path difference between adjacent rings by reducing the widths of rings and increasing the number of rings have resulted in excessive complexity and cost for a commercially acceptable system.

SUMMARY OF THE INVENTION

Accordingly, one object of this invention is to provide a novel ultrasonic system for ultrasonic imaging which overcomes the above-noted problems and derives other advantages by suppressing side lobe amplitudes in a beam profile generated by a flat annular transducer array.

Another object of this invention is to minimize errors of the time delays in an individual ring element, and to equalize substantially errors of the time delays between annular transducers.

A further object of this invention is to optimize the ultrasound beam profile with the annular transducer array, and with swept focusing by changing the relative aperture of the array.

These and other objects are achieved in accordance with the invention, by providing a novel ultrasonic system including an array of rings having a flat radiating surface, wherein the ring elements of the array have equal areas and the appropriate time delays are provided.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENT

Figure 1:
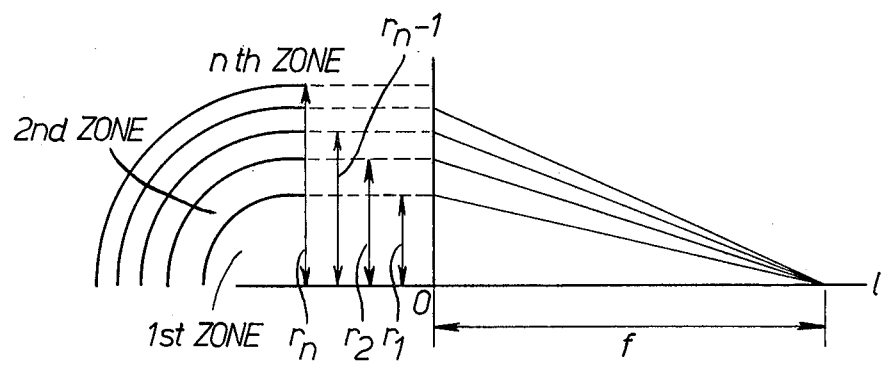
FIG. 1 is a geometric construction useful in calculating the delay time required for focusing the ultrasonic energy of an annular transducer array at any point in the aperture of the array.
Figure 3:
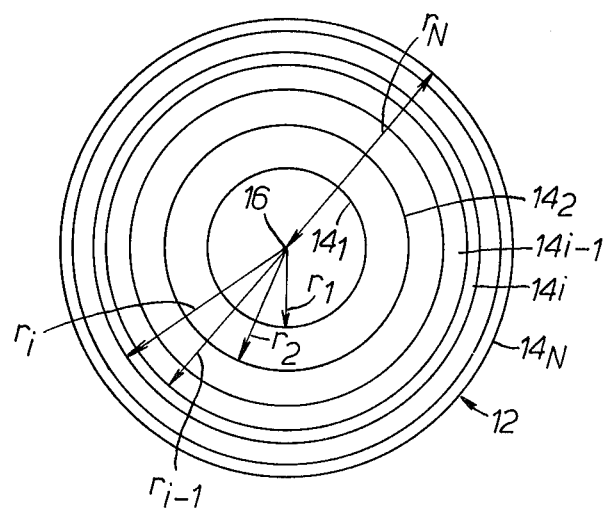
FIG. 3 is a plan view of an embodiment of the coaxial annular transducer array of FIG. 2.
Figure 2:
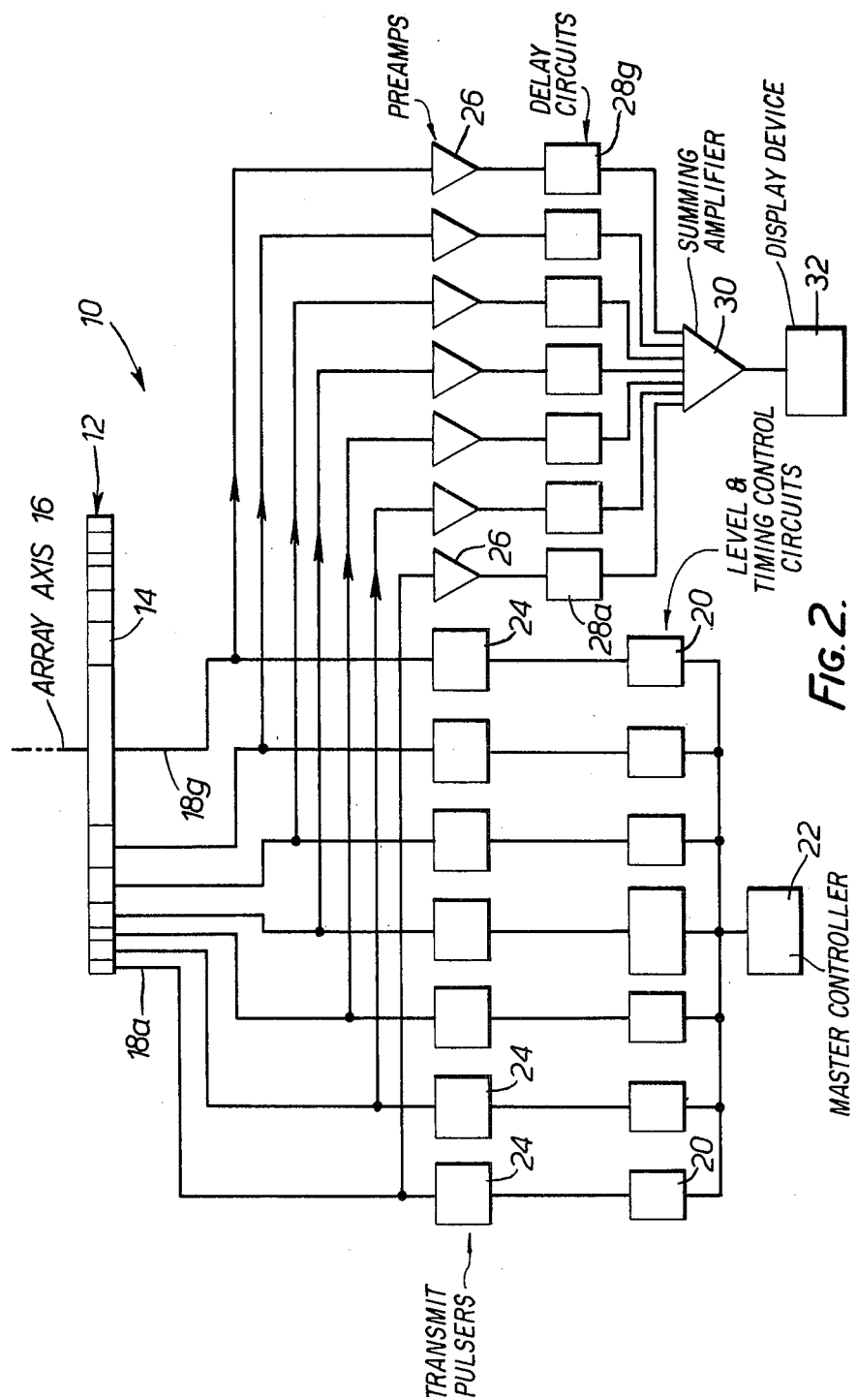
FIG. 2 is a functional block diagram of an ultrasonic system incorporating the coaxial annular transducer array embodying the present invention.

Referring now to the drawings, wherein like reference numerals designate identical or corresponding parts throughout the several views, and more particularly to FIGS. 2 and 3 thereof, the system 10 includes a planar array 12 of annular transducers 14 arranged on a common plane about a common axis 16 of the array 12. The transducers 14 may be fabricated of a piezoelectric material, such as lead-zirconate-titanate, with electrodes (not shown) attached to the material in a conventional manner. The transmitting and receiving channels 18a–18g each include a respective level and timing control circuit 20 under the control of master controller 22 for determining the level and timing of a transmit pulse generated by a respective transmit pulser 24 applied to a respective of the transducer elements.

Plural receiving channels are provided for processing the received echo electrical signals, each including a preamplifier 26 to protect the sensitive preamplifier inputs from the high transmitting voltage, and reduce the large dynamic acoustic range to a smaller range a cathode ray tube display device can handle. The amplified echo signal is nextly fed to respective delay circuits 28a–28g having an associated delay select switch (not shown) which, under the control of master controller 22, selects the delay element or elements to focus the echo signal in the delay channels. Master controller 22 can take various forms and can be a hard-wired logic circuit, but is preferably a properly programmed minicomputer or microcomputer. In operation, transducer excitation pulses are generated in time sequence to focus the generated ultrasound beam. The received echo signals are time delayed by different preselected amounts in the receiving channels. The delayed echo signals are fed to a summing amplifier 30, and summed thereby. The summing amplifier outputs are supplied to display device 32.

In accordance with the invention, the array 12 includes n coaxial annular sonic transducers 14 positioned in a plane, wherein the respective outer radii $r_1$-$r_N$ of the respective n transducers conform with the following equation:

$$r_i = (i/N)^{\frac{1}{2}} r_N \qquad (2)$$

To focus the array 12 at a depth f on the array axis 16, the time delay $t_i$ provided to the i-th transducer 14 of the array 12 is given by:

$$t_i = f/c[\{1 + (r_N/f)^2\}^{\frac{1}{2}} - \{1 + (x_i/f)^2\}^{\frac{1}{2}}] \qquad (3)$$

$$x_i = \{(i-\tfrac{1}{2})/N\}^{\frac{1}{2}} r_N \qquad (4)$$

wherein,
  $x_i$ = distance from the center of the array, and
  c = speed of sound traveling through the medium.

The advantage of using the array complying with the conditions, which are given by the equations (2), (3) and (4), arises due to suppression of the side lobe which represents the transmission or reception of the ultrasound beam in directions other than the direction of the main beam by minimizing the error of the delay time in the individual annular transducer 14, and equalization of the errors of the delay time between adjacent annular transducers.

Let us now examine the method of introduction of the conditions for an array including coaxial annular sonic transducers. The time delay $t_i$ for the i-th annular transducer 14 of the array 12 to focus the ultrasound beams generated at a depth f on the array axis is given by equation (3).

In FIG. 3, we have considered the error $e_i$ of the delay time in the i-th annular transducer 14.

The error $e_i$ of the delay time is:

$$e_i = \int_{r_{i-1}}^{r_i} |t_i - tx| \cdot 2\pi x \, dx \qquad (5)$$

$$= \pi f^3/3c[\{1 + (x/f)^2\}^{\frac{1}{2}} \{(2x^2 - 3r_{i-1}^2 - 3r_i^2)/f^2 - 4\} + 2\{1 + (r_{i-1}/f)^2\}^{3/2} + 2\{1 + (r_i/f)^2\}^{3/2}]$$

The derivative $de_i/dx$ can be obtained by implicitly differentiating equation (5), and let $de_i/dx = 0$. Then we can find that:

$$x_i(\min) = \{(r_{i-1}^2 + r_i^2)/2\}^{\frac{1}{2}} \qquad (6)$$

and the minimum error $e_i(\min)$ of the delay time is given by:

$$e_i(\min) = \pi f^2/3c[2\{1 + (r_{i-1}/f)^2\}^{3/2} + 2\{1 + (r_i/f)^2\}^{3/2} - \qquad (7)$$

$$4\{1 + (r_{i-1}^2 + r_i^2)/2f^2\}^{3/2}]$$

Thus, in order to minimize the error $e_i$ of the delay time in the i-th annular transducer element 14, the annular transducer should be energized by a pulse delayed in time from the main trigger pulse, whose delay time is determined by substituting the result x (min) given by equation (6) into equation (3).

We can now determine the outer radii $r_i$ of the respective i-th annular transducer 14 considering the following term:

$$e_{i-1}(\min) = e_i(\min) \qquad (8)$$

The above expression represents that the minimum error $e_i(\min)$ of the delay time is equal in all annular transducers of the array.

Then in the case of use of the approximation $\{1 + (r_i/f)^2\}^{\frac{1}{2}} \approx 1 + (r_i/f)^2/2$ the equation (6) can be rewritten as:

$$e_i = \pi/4cf^3\{2x^4 - 2(r_{i-1}^2 + r_i^2)x^2 + r_{i-1}^4 + r_i^4\} \qquad (9)$$

where the outer radii $r_i$ of the i-th annular transducer 14 satisfies $f \gg r_i$ for all f considered practically.

Now implicitly differentiating equation (9) and further letting $de_i/dx = 0$, we obtain the minimum error as:

$$e_i(\min) = \pi/8cf^3(r_{i-1}^2 - r_i^2)^2 \qquad (10)$$

Considering the term given by equation (8), we finally obtain the derivative of equation (10). Its derivative is $$\pi/8cf^3(r_{i-1}^2 - r_i^2)^2 = \pi/8cf^3(r_i^2 - r_{i+1}^2)^2 \qquad (11)$$

$$r_i^2 = (r_{i-1}^2 + r_{i+1}^2)^{1/2}$$

Then equation (11) becomes equation (2) for the outer radii $r_N$ of the outmost annular transducer 14N.

Substituting equation (2) into equation (6) and equation (10), we can obtain:

$$e_i(\min) = \pi/8cf^3 N^2 \cdot r_N^4 \qquad (12)$$

$$x_i(\min) = (i - \tfrac{1}{2})/N)^{\frac{1}{2}} r_N \qquad (13)$$

The relationship given by equation (11) is represented in FIG. 3, wherein the areas of the annular transducers 14 constructing the array 12 are equal. In FIG. 3, the delay time $t_i$ for the i-th annular transducer 14 controlled by master controller 22 is given by equation (3) with $x_i$ being replaced by $x_i(\min)$ given by equation (13).

Figure 4:
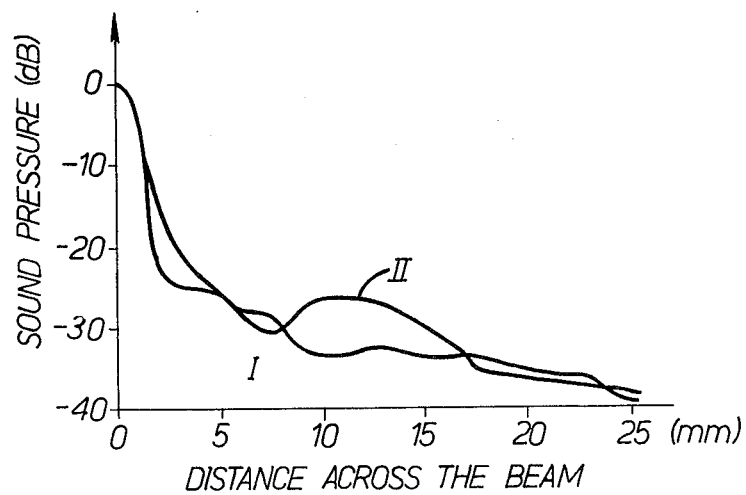
FIG. 4 is a graph illustrating sound pressure as a function of the distance across the beam achieved with the annular transducer array of the invention in comparison with the annular transducer array manufactured according to the prior art.

FIG. 4 shows the comparison of beam profiles with the annular transducer array having equal areas according to the invention and the annular transducer array having equal widths in the prior art. It has been seen clearly that beam profile for the annular transducer according to the invention as indicated as I has a significantly better characteristic in the distance range from approximately 7 mm through 16 mm than characteristics of the prior art annular transducer indicated as II. In accordance with the invention, the energy in the side lobe is much lower than that in the main lobe.

Table 1 below shows the assumed condition for the annular transducers I and II whose beam characteristics are shown diagrammatically in FIG. 4. The areas of the annular transducers in the array I are all 50.24 mm².

TABLE 1

|  | Transducer Array I | | Transducer Array II | |
| --- | --- | --- | --- | --- |
|  | Radial Width | Outer Radii | Radial Width | Outer Radii |
| element 1 | 4.0 | 4.0 | 1.8 | 1.8 |
| 2 | 1.7 | 5.7 | 1.8 | 3.6 |
| 3 | 1.3 | 7.0 | 1.8 | 5.4 |
| 4 | 1.1 | 8.1 | 1.8 | 7.2 |
| 5 | 0.9 | 9.0 | 1.8 | 9 |

Figure 5:
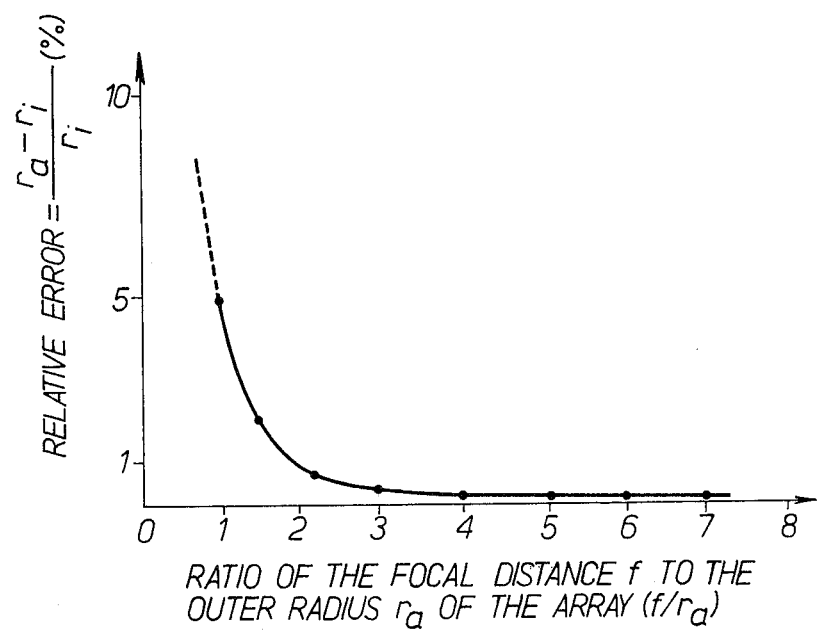
FIG. 5 is a graph illustrating the relative error between exact solution and approximate solution for the annular transducer as a function of the ratio of focal distance divided by the exact solution.

The diagram of FIG. 5 shows the plots of the relative error between exact solution $r_a$ and approximate solution $r_i$ given by equation (2) for the outer radii of the i-th transducer as a function of the ratio $f/r_a$, focal distance f divided by the exact radius $r_a$. The radius $r_i$ given by equation (2) using the approximation is equal in accuracy within 1% of results obtained using the equation of the sixth degree with respect to $r_a$ exactly in the range $f/r_a > 3$, as seen in FIG. 5.

Figure 6:
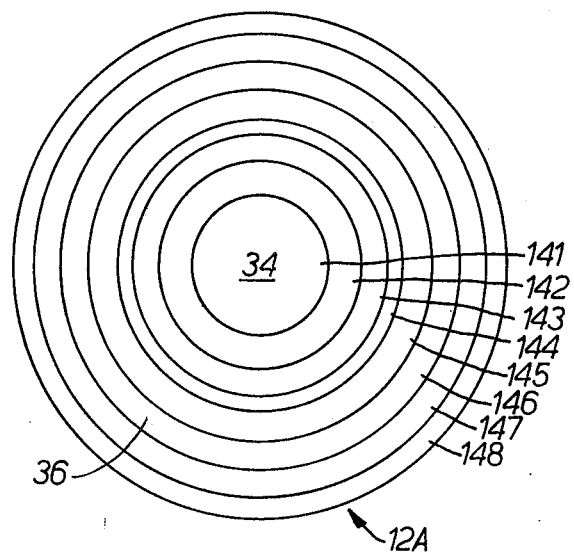
FIG. 6 is a front view of an array of coaxial annular transducers in an alternative embodiment of the array of FIG. 3.

Referring now to FIG. 6, there is seen an annular transducer array 12A which is an alternative embodiment of the array 12 of FIGS. 2 and 3. The array 12A includes an inner region 34, and an outer region 36. In the inner region 34, the four annular transducers 141–144 are arranged on a common plane about a common axis 16 and have the same areas A34, and in the outer region 36 the four annular transducers 145–148 are arranged on the common plane about the common axis 16, and have the same areas A36 larger than that in the region 34. The region 34 and region 36 are selectively energized to change the relative aperture of the array 12, so that the focal range is changed progressively.

It is possible to accomplish the purpose of optimizing beam size throughout both the near-field and the far-field in the ultrasound transition range by controlling the effective aperture of the array as a function of the distance of the medium.

Figure 7:
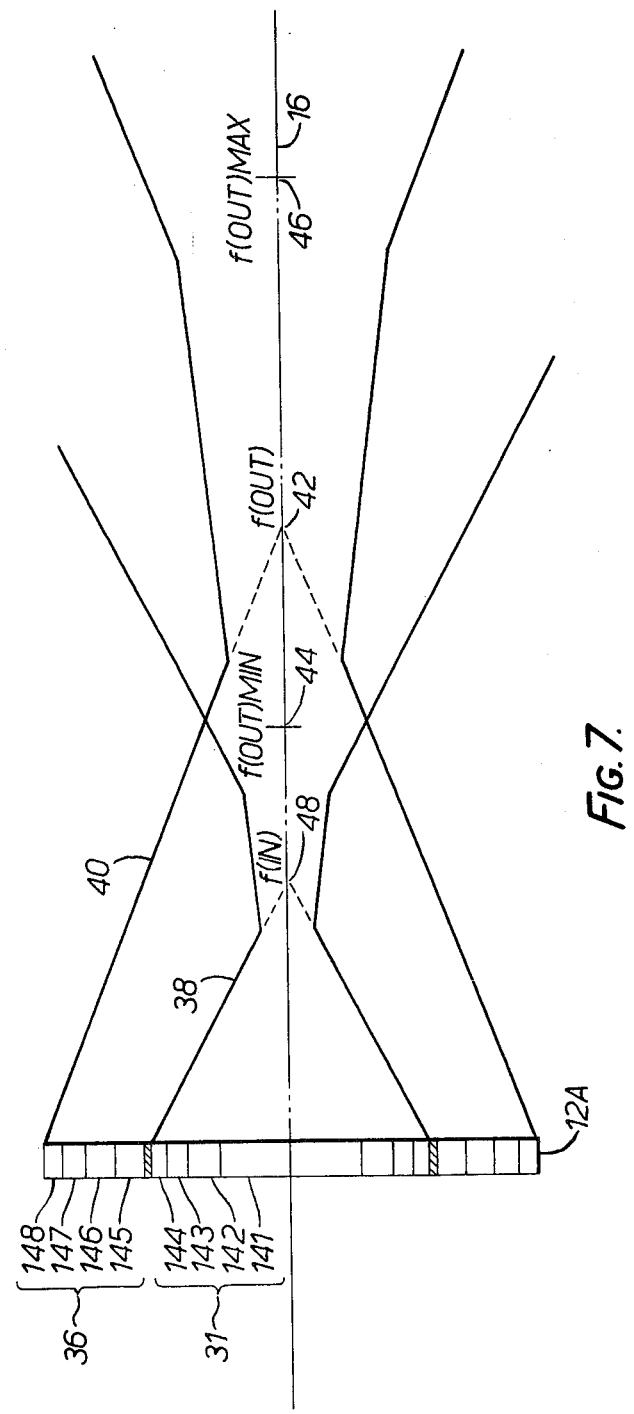
FIG. 7 is a diagram illustrating the outline of beams produced by the annular transducers array according to the present invention.

In an ultrasonic imaging system used for imaging the medium, reflecting objects may be in either the near-field or the far-field region. When looking in the medium in the near-field, the annular transducers 145–148 of the region 36 of array 12 are deenergized. At great distances the entire array 12 is utilized to get the smallest possible beam size to achieve the best lateral resolution. FIG. 7 illustrates the outlines of the beam produced by the annular transducer array 12A. The beam 38 in the near-field of the smallest active array is smaller than the beam 40 from the full-sized array. The near-field of the small array is considerably shorter than that of the large array and the far-field beam is correspondingly larger.

Thus the annular transducer elements in the array are successively connected to produce the smallest possible beam size for the particular distance being observed.

For illustrative purposes in explaining the operation of the alternative embodiment, it is assumed that the minimum width of the annular transducer arranged in each of the regions is constant. With this assumption, the minimum width Wmin of the annular transducer in the outer region is give by:

$$W_{min} = r_{(out)m} - r_{(out)m-1} \quad (14)$$

Where $r_{outmost}$ = the outer radius of the outermost annular transducer $$m_{(out)} = (r_{outmost})^2 / \{W_{min}(2r_{outmost} - W_{min})\} \quad (15)$$

= an integer rounded to the nearest whole number.

Then, the radius $r_{(out)i}$ for the i-th annular transducer of the outer region is:

$$r_{(out)i} = \{(i/m_{out})\}^{\frac{1}{2}} r_{(outmost)} \quad (16)$$

and it is further assumed that the error ei of the delay time in each region, so that the minimum of the error ei (min) is given by:

$$ei_{(min)} = (\pi/8cf_{(out)}m^2_{(out)})(r_{(outmost)})^4 \quad (17)$$

where $f_{(out)}$min = the nearest focal distance focused by the entire array under control of the master controller 32;

$f_{(out)}$max = the farthest focal distance focused by the entire array under control of the master controller 22; and $f_{(out)}$ satisfies $f(out)min \leq f_{(out)} \leq f_{(out)max}$.

Referring also to the diagram of FIG. 7, and with reference to the case of the outer region of the array 12A, the focusing at the respective focal point $f_2(f_{(inn)} < f_{(out)min})$ is accomplished, as has been noted hereinabove, by de-energizing the outer region of the array 12 to change the effective aperture of the array and by appropriately changing the delay time introduced by the master controller 22.

The radius $r_{(inn)i}$ for the i-th annular transducer of the inner region of the array 12A is given by:

$$r_{(inn)i} = (i/m_{(inn)})^{\frac{1}{2}} r_{(inn)}$$

where r(inn) = the largest radius of the annular transducer of the inner region $$m_{(inn)} = (r_{inn})^2 / \{W_{min}(2r_{inn} - W_{min})\} \quad (18)$$

= an integer rounded to the nearest whole number.

If the number of the annular transducers whose radii are smaller than $r_{inn}$ in the outer region is $m_c$, the radii of the respective $m_{(out)}$th through $m_{(out)} - m_c + m_{(inn)}$th are give by equation (18).

Each of the regions of the array 12A provides a focusing of the ultrasound beam from each of the regions to the respective focal points 42–48 on the array axis 16 shown in FIG. 7 by the use of the delay circuits.

Then, the delay time $t_i$ provided to the i-th annular transducer whose radius $r_i$ satisfies $r_{(inn)} \leq r_i < r_{outmost}$ is given by:

$$t_i = f_{(out)}/c\{1 + (r_{outmost}/f_{(out)})^2\}^{1/2} - \{1 + (x_i/f_{(out)})^2\}^{1/2} \quad (19)$$

wherein, $$x_i = \{(i - 1/2)/m_{(out)}\}^{1/2} r_{outmost} \quad (20)$$

In general, if J is the number of the stages of changing the effective aperture of the array progressively, the delay time $t_i$ provided to the i-th annular transducer whose radius $r_i$ satisfies $r^{(j+1)} \leq r_i \leq r^{(j)}$ is given by:

$$t_i = f_{(out)}/c\{1 + (r^{(j)}/f_{(out)})^2\}^{\frac{1}{2}} - \{1 + (x_i/f_{(out)})^2\}^{\frac{1}{2}} \quad (21)$$

where $r^{(j)}$ = the largest radius of the annular transducer in the $j$-th effective aperture changed $r^{(j+1)}$ = the largest radius of the annular transducer in the $(j+1)$th effective aperture $$x_i = \{(i - 1/2)/m^{(j)}\}^{1/2} r^{(j)} \qquad (22)$$

since $$m^{(j)} = (r^{(j)})^2/\{W_{min}(2r^{(j)} - W_{min})\}$$

= an integer rounded to the nearest whole number.

Alternatively, the transducers 141–144 of the region 34 are energized with individual values of delay time to focus an ultrasound beam emanating from the small effective aperture about the near focal point 48 shown in FIG. 7. Thus, the delay time $t_i$ for the i-th annular transducer satisfying $r^{(j+1)} \leq r_i \leq r^{(j)}$ is given by:

$$t_i = f_{(inn)}/c\{1 + (r^j/f_{(min)})^2\}^{1/2} - \{1 + (x_i/f_{(inn)})^2\}^{1/2} \qquad (23)$$

In the same way, if K is the number of the stages of changing the effective aperture of the array progressively, the delay time $t_i$ provided to the i-th annular transducer whose radius $r_i$ satisfies $r^{(k+1)} \leq r_i \leq r^{(k)} \leq r^{(j)}$ is given by:

$$t_i = f_{(inn)}^{(K)}/c\{1 + (r^{(k)}/f_{(inn)}^{(K)})^2\}^{1/2} - \{1 + (x_i/f_{(inn)}^{(K)})^2\}^{1/2} \qquad (24)$$

wherein, $r^{(k)}$ = the largest radius of the annular transducer in the $k$-th effective aperture changed $r^{(k+1)}$ = the largest radius of the annular transducer in the $(k+1)$th effective aperture $$x_i = \{(i - 1/2)/m^{(k)}\}^{1/2} r^{(k)} \qquad (25)$$

since $$m^{(k)} = (r^{(k)})^2/\{W_{min}(2r^{(k)} - W_{min})\}$$

= an integer sounded to the nearest whole number

An annular transducer array manufactured according to the invention is shown in FIGS. 6 and 7.

The radius values corresponding to the example given in FIGS. 6–7 are identified in the following Table B:

TABLE B

| element | outer radius |
|---|---|
| 148 | 12 |
| 147 | 10.95 |
| 146 | 9.8 |
| 145 | 8.49 |
| 144 | 6.9 |
| 143 | 5.98 |
| 142 | 4.88 |
| 141 | 3.45 |

For example, it is assumed that the inner region 34 including annular transducers 141–144 is activated for distance in the range of 0 to 80 mm, and the inner region 34 and the outer region 36 are activated for distances in the range of 80 to 180 mm with the dynamic focusing to change the focal spots along the axis of the array.

Figure 8:
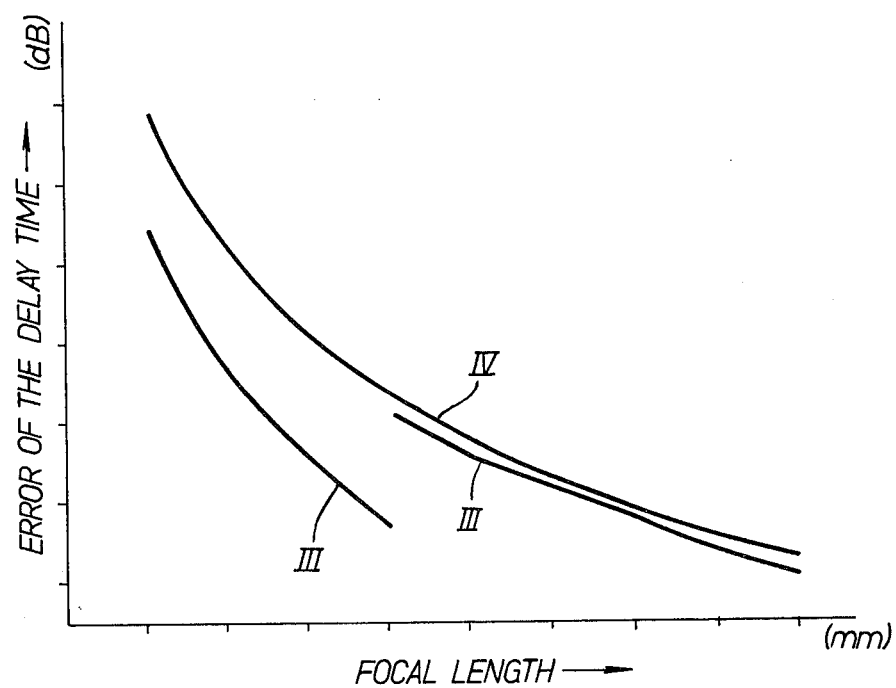
FIG. 8 is a graph illustrating the error of the delay time as a function of the focal length achieved with the annular transducers array in accordance with the present invention in comparison with the conventional annular transducer array.

The diagram of the FIG. 8 show the plots of the error of the delay time as a function of the focal length. In FIG. 8, the error of the delay time for the transducer array with changing the effective aperture of the array with the dynamic focusing as indicated as III is more suppressed than that of the conventional transducer array having a plurality of the same width annular transducer elements indicated as IV.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An ultrasonic system for ultrasonic imaging, comprising:
   an array defining an axis and including a plurality of flat annular transducer elements arranged contiguously in concentric relation and in a common plane for transmitting ultrasonic sound waves to an object in a medium and for receiving ultrasonic sound waves reflected therefrom, each of said transducer elements having substantially the same area;
   pulse generating means for applying high frequency electrical pulses to said transducer elements of said array;
   control means for successively energizing said transducer elements so as to create a focus of focal maximum intensity having a predetermined ultrasonic sound beam profile at a predetermined point in a predetermined region of said medium, comprising means for varying a relative time delay between the pulses applied to said transducer elements to minimize error of delay time of ultrasonic energy transmission and reception in each individual transducer element and to equalize errors in delay time between adjacent transducer elements;
   means for summing the plurality of received ultrasonic signals from said array; and
   means for displaying ultrasonic image in correspondence with the summed signals;
   wherein the radius of the i-th transducer element as measured from the axis of the array is given in accordance with the relation:

$$r_i = (i/N)^{\frac{1}{2}} r_N$$

wherein N is the number of coaxial annular transducer elements and $r_N$ is the outer radius of the outermost annular transducer element; and
   wherein the relative time delay T of energization of the i-th annular transducer element is determined by the means for varying a relative time delay according to the following relationships:

$$T_i = f/c[\{1 + (r_N/f)^2\}^{\frac{1}{2}} - \{1 + (x_i/f)^2\}^{\frac{1}{2}}]$$

$$x_i = \{(i-\tfrac{1}{2})1/N\}^{\frac{1}{2}} r_N$$

where f is the focal length along the axis of the array, and c is the velocity of the ultrasonic sound wave.

2. An ultrasonic system for ultrasonic imaging, comprising:

an array defining an axis and including a plurality of flat annular transducer elements arranged in concentric relation and in a common plane for transmitting ultrasonic sound waves to an object in a medium and for receiving ultrasonic sound waves reflected therefrom, said transducer elements being grouped into at least two sections which respectively focus ultrasonic beams in inner and outer regions, wherein the transducer elements of each section each have substantially the same area;

pulse generating means for applying high frequency electrical pulses to said transducer elements of said array;

control means for selectively energizing or deenergizing the transducer elements of each said section in correspondence with a predetermined focal length, comprising means for applying a variable relative time delay to respective transducer elements to minimize error of time delay of ultrasonic energy transmission and reception of each individual transducer element and to equalize errors in delay time between adjacent transducer elements in each said section so as to create a focus of focal maximum intensity at a predetermined point in a predetermined region of said medium;

means for summing the plurality of received ultrasonic signals from said array; and means for displaying ultrasonic image in correspondence with the summed signals;

wherein the radius of the i-th transducer element as measured from the axis of the array in each said section of the array is given in accordance with the relation:

$$r_i = (i/M)^{\frac{1}{2}} r_L$$

where M is the respective number of coaxial annular transducer elements in each section, and $r_L$ is the respective largest outer radius of the annular transducer element in each section; and wherein the relative time delay T of energization of the i-th annular transducer element is determined by said means for applying a variable relative time delay according to the following relationships:

$$T_i = F/c[\{1+(r_L/F)^2\}^{\frac{1}{2}} - \{1+(x_i/F)^2\}^{\frac{1}{2}}]$$

$$x_i = \{(i-\tfrac{1}{2})1/M\}^{\frac{1}{2}} r_L$$

where F is the focal length at the focal spot along the axis of the array formed by each set of annular transducer element, and c is the velocity of the ultrasonic sound wave.

* * * * *